US007927857B2

(12) United States Patent
Nielsen et al.

(10) Patent No.: US 7,927,857 B2
(45) Date of Patent: *Apr. 19, 2011

(54) GLUCOAMYLASE VARIANTS

(75) Inventors: Bjarne Ronfeldt Nielsen, Virum (DK);
Allan Svendsen, Horsholm (DK);
Henrik Pedersen, Bagsvaerd (DK);
Jesper Vind, Lyngby (DK); Hanne Vang Hendriksen, Holte (DK); Torben Peter Frandsen, Frederiksberg C (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/034,906

(22) Filed: Feb. 21, 2008

(65) Prior Publication Data

US 2008/0213843 A1 Sep. 4, 2008

Related U.S. Application Data

(63) Continuation of application No. 10/421,586, filed on Apr. 23, 2003, now Pat. No. 7,354,753, which is a continuation of application No. 09/612,489, filed on Jul. 7, 2000, now abandoned.

(60) Provisional application No. 60/143,313, filed on Jul. 12, 1999.

(30) Foreign Application Priority Data

Jul. 9, 1999 (DK) .................................. 1999 00999

(51) Int. Cl.
*C12N 9/00* (2006.01)
*C12N 9/34* (2006.01)
*C12N 1/20* (2006.01)
*C12N 15/00* (2006.01)
*C07H 21/04* (2006.01)

(52) U.S. Cl. ...................... 435/205; 435/183; 435/252.3; 435/320.1; 536/23.2

(58) Field of Classification Search ......................... None
See application file for complete search history.

(56) References Cited

U.S. PATENT DOCUMENTS

| 5,162,210 | A | 11/1992 | Sierks et al. |
| 5,665,585 | A | 9/1997 | Torkkeli et al. |
| 6,255,084 | B1 | 7/2001 | Nielsen et al. |
| 6,329,186 | B1 | 12/2001 | Nielsen et al. |
| 6,352,851 | B1 | 3/2002 | Nielsen et al. |
| 6,620,924 | B2 | 9/2003 | Nielsen et al. |
| 7,060,468 | B2 | 6/2006 | Nielsen et al. |
| 7,122,365 | B2 | 10/2006 | Nielsen et al. |
| 7,129,069 | B2 | 10/2006 | Borchert et al. |

FOREIGN PATENT DOCUMENTS

| WO | WO 92/00381 | 1/1992 |
| WO | WO 98/03639 | 1/1998 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hata et al., EMBL entry AMYG__ASPOR published in 1991.
Hata et al., UNIPROT Database, Accession Nos. P36914 and Q3HLW7 (1991).
Boel et al., The EMBO Journal, vol. 3, No. 5, pp. 1097-1105 (1984).
Chen Hsiu-Mei, "Site-Directed Mutagenesis to Enhance" Kun Abstract.
Hata et al., GenBank Acc No. JC6538 (1998).
Vainio et al., GenBank Acc No. S33908 (1993).
Shibuya et al., GenBank Acc No. JQ0607 (1992).
Hayashida et al., GenBank Acc No. JT0479 (1990).
Shibuya et al., GenBank Acc No. P22832 (1991).
Diagne et al., GenBank Acc No. Q12537 (1996).
Sierks et al., "Catalytic Mechanism Of Fungal Glucoamylase As Defined By Mutagenesis Of Asp176, Glu179 and Glu180 In The Enzyme From *Aspergillus awamori*", Protein Engineering, vol. 3, pp. 193-198 (1990).
Sierks et al., "Site-Directed Mutagenesis At The Active Site Trp120 Of *Aspergillus awamori* Glucoamylase", Protein Engineering, vol. 2, pp. 621-625 (1989).
Li et al., "Effect Of Introducing Proline Residues On The Stability Of *Aspergillus awamori*", Protein Engineering, vol. 10, pp. 1199-1204 (1997).
Fierobe et al., "Mutational Modulation Of Substrate Bond-Type Specificity And Thermostability Of Glucoamylase From *Aspergillus awamori* By Replacement With Short Homologue Active Site Sequences . . . ", Biochemistry, vol. 35, pp. 8698-8704 (1996).
Aleshin et al., "Crystal Structure Of Glucoamylase From *Aspergillus awamori* Var. X100 To 2.2-Å Resulution", Journal of Biological Chemistry, vol. 267 pp. 19291-19298 (1992).
Aleshin et al., "Crystallographic Complexes Of Glucoamylase With Maltooligosaccharide Analogs: Relationship", Biochemistry, vol. 35, pp. 8319-8328 (1996).
Svensson et al., "The Complete Amino Acid Sequence Of The Glycoprotein, Glucoamylase G1, From *Aspergillus niger*", Carlsberg Research Communications, vol. 48, pp. 529-544 (1983).
Berland et al., "Thermodynamics Of Inhibitor Binding To Mutant Forms Of Glucoamylase From *Aspergillus niger* Determined By Isothermal Titration Calorimetry", Biochemistry, vol. 34, pp. 10153-10161 (1995).
Frandsen et al., "Mutational Analysis Of The Roles In Catalysis And Substrate Recognition Of Arginines 54 and 305, Aspartic Acid 309, And Tryptophan 317 Located At Subsites 1 And 2 In Glucoamylase From *Aspergillus niger*" Biochemistry, vol. 34, pp. 10162-10169 (1995).
Harris et al., "Refined Structure For The Complex Of 1-Deoxynojirimycin With Glucoamylase From *Aspergillus awamori* Var. X100 To 2.4-Å Resulution", Biochemistry, vol. 32, pp. 1618-1626 (1993).

(Continued)

*Primary Examiner* — Christian L Fronda
(74) *Attorney, Agent, or Firm* — Elias Lambiris

(57) ABSTRACT

The invention relates to a variant of a parent fungal glucoamylase, which exhibits altered properties, in particular improved thermal stability and/or increased specific activity.

14 Claims, 1 Drawing Sheet

OTHER PUBLICATIONS

Frandsen et al. "Site-Directed Mutagenesis Of The Catalytic Base Glutamic Acid 400 In Glucoamylase From *Aspergillus niger* And Of Tyrosine 48 And Glutamine 401, Both Hydrogen-Bonded To The Y-Carboxylate Group Of Gluta . . . ", Biochemistry, vol. 33, pp. 13808-13816 (1994).

Chen et al., "Effect of Replacing Helical Glycine Residues With Alanines On Reversible And Irreversible Stability And Production Of *Aspergillus awamori* Glucoamylase", Protein Engineering, vol. 9, pp. 499-505 (1996).

Chen et al., "Identification And Elimination By Site-Directed Mutagenesis Of Thermolabile Aspartyl Bonds In *Aspergillus awamori* Glucoamylase", Protein Engineering, vol. 8, pp. 575-582 (1995).

Chen et al, "Substitution Of Asparagine Residues In *Aspergillus awamori* Glucoamylase By Site-Directed Mutagenesis To Eliminate N-Glycosylation And Inactivation By Deamidation", Biochemical Journal, vol. 301, pp. 275-281 (1994).

Svensson et al., "Characterization Of A Glucoamylase G2 From *Aspergillus niger*", European Journal of Biochemistry, vol. 154, pp. 497-502 (1986).

Yu et al., "Program Enzyme Engineering Xiv Chaired by Yu et al., Beijing, China", Engineering Foundation Conferences (1997).

Li Yuxing, "Genetic Construction And Biochemical Analysis Of Thermostability Mutants Of Glucoamylase From *Aspergillus awamori*" Kun Abstract, (1996).

\* cited by examiner

GLUCOAMYLASE VARIANTS

CROSS-REFERENCE TO RELATED APPLICATIONS

This application is a continuation of U.S. application Ser. No. 10/421,586 filed Apr. 23, 2003, now U.S. Pat. No. 7,354,753, which is a continuation of U.S. application Ser. No. 09/612,489 filed Jul. 7, 2000, now abandoned, and claims the benefit under 35 U.S.C. 119 of U.S. provisional application No. 60/143,313 filed Jul. 12, 1999,and priority of Danish application no. PA 1999 00999, filed Jul. 9, 1999, the contents of which are fully incorporated herein by reference.

FIELD OF THE INVENTION

The present invention relates to novel glucoamylase variants (mutants) of parent AMG with altered properties, in particular with improved thermal stability and/or increased specific activity, which variants are, e.g., suitable for starch conversion, in particular for producing glucose from starch, and for ethanol production, sweetener production. More specifically, the present invention relates to glucoamylase variants and the use of such variant enzymes.

BACKGROUND OF THE INVENTION

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi or yeasts, with those from *Aspergillus* being commercially most important.

Commercially, the glucoamylase enzyme is used to convert cornstarch, which is already partially hydrolyzed by an alpha-amylase to glucose. The glucose is further converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced.

One of the main problems exist with regard to the commercial use of glucoamylase in the production of high fructose corn syrup is the relatively low thermal stability of glucoamylase. Glucoamylase is not as thermally stable as alpha-amylase or glucose isomerase and it is most active and stable at lower pH's than either alpha-amylase or glucose isomerase. Accordingly, it must be used in a separate vessel at a lower temperature and pH.

Glucoamylase from *Aspergillus niger* has a catalytic (aa 1-440) and a starch binding domain (aa 509-616) separated by a long and highly O-glycosylated linker (Svensson et al. (1983), *Carlsberg Res. Commun.* 48, 529-544, 1983 and (1986), *Eur. J. Biochem.* 154, 497-502). The catalytic domain (aa 1-471) of glucoamylase from *A. awamori* var. X100 adopt an $(\alpha/\alpha)_6$-fold in which six conserved $\alpha \rightarrow \alpha$ loop segments connect the outer and inner barrels (Aleshin et al. (1992), *J. Biol. Chem.* 267, 19291-19298). Crystal structures of glucoamylase in complex with 1-deoxynojirimycin (Harris et al. (1993), *Biochemistry*, 32, 1618-1626) and the pseudotetrasaccharide inhibitors acarbose and D-gluco-dihydroacarbose (Aleshin et al. (1996), *Biochemistry* 35, 8319-8328) furthermore are compatible with glutamic acids 179 and 400 acting as general acid and base, respectively. The crucial role of these residues during catalysis have also been studied using protein engineering (Sierks et al. (1990), *Protein Engng.* 3, 193-198; Frandsen et al. (1994), *Biochemistry,* 33, 13808-13816). Glucoamylase-carbohydrate interactions at four glycosyl residue binding subsites, −1, +1, +2, and +3 are highlighted in glucoamylase-complex structures (Aleshin et al. (1996), *Biochemistry* 35, 8319-8328) and residues important for binding and catalysis have been extensively investigated using site-directed mutants coupled with kinetic analysis (Sierks et al. (1989), *Protein Engng.* 2, 621-625; Sierks et al. (1990), *Protein Engng.* 3, 193-198; Berland et al. (1995), *Biochemistry,* 34, 10153-10161; Frandsen et al. (1995), *Biochemistry,* 34, 10162-10169.

Different substitutions in *A. niger* glucoamylase to enhance the thermal stability have been described: i) substitution of alpha-helical glycines: G137A and G139A (Chen et al. (1996), *Prot. Engng.* 9, 499-505); ii) elimination of the fragile Asp-X peptide bonds, D257E and D293E/Q (Chen et al. (1995), *Prot. Engng.* 8, 575-582); prevention of deamidation in N182 (Chen et al. (1994), *Biochem. J.* 301, 275-281); iv) engineering of additional disulphide bond, A246C (Fierobe et al. (1996), *Biochemistry,* 35, 8698-8704; and v) introduction of Pro residues in position A435 and S436 (Li et al. (1997), *Protein Engng.* 10, 1199-1204. Furthermore Clark Ford presented a paper on Oct. 17, 1997, ENZYME ENGINEERING 14, Beijing/China Oct. 12-17, 1997, Abstract number: Abstract book p. 0-61. The abstract suggests mutations in positions G137A, N20C/A27C, and S30P in (not disclosed) *Aspergillus awamori* glucoamylase to improve the thermal stability.

Additional information concerning glucoamylase can be found on an Internet homepage (http://www.public.iastate.edu/~pedro/glase/glase.html)

"Glucoamylase WWW page" (Last changed Oct. 8, 1997) by Pedro M. Coutinho discloses informations concerning glucoamylases, including glucoamylases derivable from *Aspergillus* strains. Chemical and site-directed modifications in the *Aspergillus niger* glucoamylase are listed.

BRIEF DISCLOSURE OF THE INVENTION

The object of the present invention is to provide glucoamylase variants suitable for used in, e.g., the saccharification step in starch conversion processes.

A term "a thermostable glucoamylase variant" means in the context of the present invention a glucoamylase variant, which has a higher $T_{1/2}$ (half-time) in comparison to a corresponding parent glucoamylase. The determination of T½ (Method I and Method II) is described below in the "Materials & Methods" section.

The term "a glucoamylase variant with increased specific activity" means in the context of the present invention a glucoamylase variant with increased specific activity towards the alpha-1,4 linkages in the saccharide in question. The specific activity is determined as $k_{cat}$ or AGU/mg (measured as described below in the "Materials & Methods" section). An increased specific activity means that the $k_{cat}$ or AGU/mg values are higher when compared to the $k_{cat}$ or AGU/mg values, respectively, of the corresponding parent glucoamylase.

The inventors of the present invention have provided a number of variants of a parent glucoamylase with improved thermal stability and/or increased specific activity. The improved thermal stability is obtained by mutating, e.g., by substituting and/or deleting, inserting selected positions in a parent glucoamylase. This will be described in details below.

Nomenclature

In the present description and claims, the conventional one-letter and three-letter codes for amino acid residues are used.

For ease of reference, AMG variants of the invention are described by use of the following nomenclature:
Original amino acid(s):position(s):substituted amino acid(s)
According to this nomenclature, for instance the substitution of alanine for asparagine in position 30 is shown as:
   Ala30Asn or A30N
a deletion of alanine in the same position is shown as:
   Ala30* or A30*
and insertion of an additional amino acid residue, such as lysine, is shown as:
   Ala30AlaLys or A30AK
A deletion of a consecutive stretch of amino acid residues, such as amino acid residues 30-33, is indicated as (30-33)* or Δ(A30-N33).

Where a specific AMG contains a "deletion" in comparison with other AMG and an insertion is made in such a position this is indicated as:
   *36Asp or *36D
for insertion of an aspartic acid in position 36
Multiple mutations are separated by plus signs, i.e.:
   Ala30Asp+Glu34Ser or A30N+E34S
representing mutations in positions 30 and 34 substituting alanine and glutamic acid for asparagine and serine, respectively. Multiple mutations may also be separated as follows, i.e., meaning the same as the plus sign:
   Ala30 Asp/Glu34Ser or A30N/E34S
When one or more alternative amino acid residues may be inserted in a given position it is indicated as
   A30N,E or A30N/E, or A30N or A30E
Furthermore, when a position suitable for modification is identified herein without any specific modification being suggested, it is to be understood that any amino acid residue may be substituted for the amino acid residue present in the position.

Thus, for instance, when a modification of an alanine in position 30 is mentioned, but not specified, it is to be understood that the alanine may be deleted or substituted for any other amino acid, i.e., any one of:
R, N, D, A, C, Q, E, G, H, I, L, K, M, F, P, S, T, W, Y, V.

DETAILED DISCLOSURE OF THE INVENTION

Figure 1:
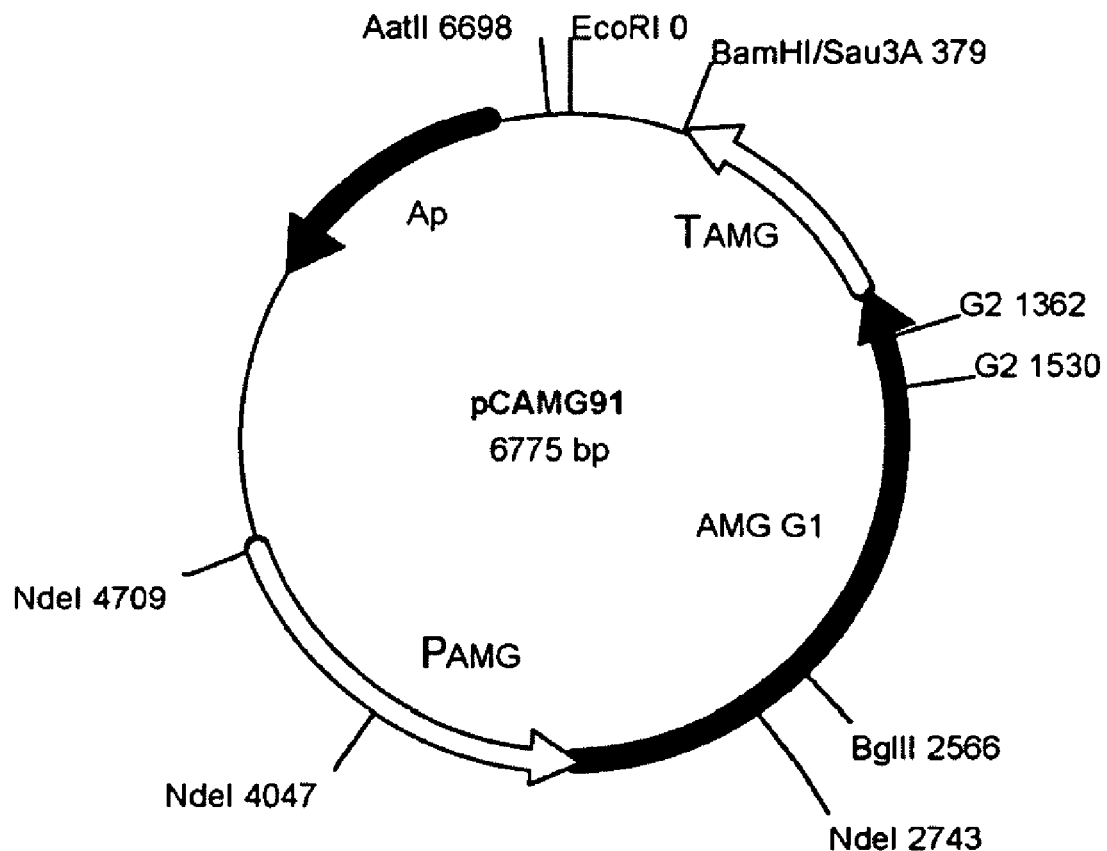
FIG. 1 shows the plasmid pCAMG91 containing the Aspergillus niger G1 glucoamylase gene.

A goal of the work underlying the present invention was to improve the thermal stability and/or increase the specific activity of particular glucoamylases, which are obtainable from fungal organisms, in particular strain of the Aspergillus genus and which themselves had been selected on the basis of their suitable properties in, e.g., starch conversion or alcohol fermentation.

In this connection, the present inventors have surprisingly found that it is in fact possible to improve the thermal stability and/or increased specific activity of parent glucoamylases by modification of one or more amino acid residues of the amino acid sequence of the parent glucoamylase. The present invention is based on this finding.

Accordingly, in a first aspect the present invention relates to a variant of a parent glucoamylase comprising one or more mutations in the positions described further below.

Parent Glucoamylases

Parent glucoamylase contemplated according to the present invention include wild-type glucoamylases, fungal glucoamylases, in particular fungal glucoamylases obtainable from an *Aspergillus* strain, such as an *Aspergillus niger* or *Aspergillus awamori* glucoamylases and variants or mutants thereof, homologous glucoamylases, and further glucoamylases being structurally and/or functionally similar to SEQ ID NO:2. Specifically contemplated are the *Aspergillus niger* glucoamylases G1 and G2 disclosed in Boel et al. (1984), "Glucoamylases G1 and G2 from *Aspergillus niger* are synthesized from two different but closely related mRNAs", EMBO J. 3 (5), p. 1097-1102. The G2 glucoamylase is disclosed in SEQ ID NO: 2. In another embodiment the AMG backbone is derived from *Talaromyces*, in particular *T. emersonii* disclosed in WO 99/28448 (See SEQ ID NO: 7 of WO 99/28448).

Commercial Parent Glucoamylases

Contemplated commercially available parent glucoamylases include AMG from Novo Nordisk, and also glucoamylase from the companies Genencor, Inc. USA, and Gist-Brocades, Delft, The Netherlands.

Glucoamylase Variants of the Invention

In the first aspect, the invention relates to a variant of a parent glucoamylase, comprising an alteration at one or more of the following positions: 59, 66, 72, 119, 189, 223, 227, 313, 340, 342, 352, 379, 386, 393, 395, 402, 408, 416, 425, 427, 444, 486, 490, 494,
wherein (a) the alteration is independently
   i) an insertion of an amino acid downstream of the amino acid which occupies the position,
   (ii) a deletion of the amino acid which occupies the position, or
   iii) a substitution of the amino acid which occupies the position with a different amino acid,
(b) the variant has glucoamylase activity and (c) each position corresponds to a position of the amino acid sequence of the parent glucoamylase having the amino acid sequence of SEQ ID NO: 2.

Further, the invention relates to a variant of a parent glucoamylase which parent glucoamylase has an amino acid sequence which has a degree of identity to the amino acid sequence of SEQ ID NO: 2 of at least about 65%, preferably at least about 70%, more preferably at least about 80%, even more preferably at least about 90%, most preferably at least about 95%, and even most preferably at least about 97%.

The invention also relates to a variant of a parent glucoamylase, comprising one or more of the following: V59A, L66V/R, T72I, S119P, I189T, Y223F, F227Y, N313G, S340G, E342A, R, D, N, C, Q, G, H, I, L, K, M, F, P, S, T, W, Y, V, preferably E342T, K352R, S356G, T379A, S386K, N, R, P, A393R, S395R, Y402F, E408R, T416A, R, D, N, C, Q, G, H, I, L, K, M, F, P, S, E, W, Y, V preferably T416H, A425T, N427S/M, S444G, S486G, T490A, T494P/A, wherein (a) the variant has glucoamylase activity and (b) each position corresponds to a position of the amino acid sequence of the parent glucoamylase having the amino acid sequence of SEQ ID NO: 2.

Specific combinations of mutations include:
L66R+Y402F+N427S+S486G+A1V; N427M+S44G+V470M+T2K+S30P;
T416H+Y402F+312Q+S119P; A425T+E408R+E386K+A495T;
T379A+T2E+S386K+A393R; S386N+E408R; L66V+T2R+S394P+Y402F+RL;
S386R+T2R+A393R; I189T+Y223F+F227Y+S119P+Y402F;

S386P+S340G+D357S+T360V; V59A+S119P; V59A+N313G; V59A+A393R;
V59A+Y402F; V59A+E408R; V59A+S119P+N313G; V59A+N313G+A393R;
V59A+A393R+Y402F; V59A+Y402F+E408R; V59A+S119P+N313G+A393R;
V59A+N313G+A393R+Y402F; V59A+A393R+Y402F+E408R;
V59A+S119P+N313G+A393R+Y402F; V59A+N313G+A393R+Y402F+E408R;
V59A+S119P+L66R; V59A+S119P+S340G; V59A+S119P+S395R;
V59A+S119P+L66R+S340G; V59A+S119P+S340G+S395R;
V59A+S119P+S395R+L66R; V59A+S119P+S395R+L66R+S340G;
V59A+N313G+L66R; V59A+N313G+S340G; V59A+N313G+S395R;
V59A+N313G+L66R+S340G; V59A+N313G+S340G+S395R;
V59A+N313G+S395R+L66R; V59A+N313G+S395R+L66R+S340G;
V59A+A393R+L66R; V59A+A393R+S340G; V59A+A393R+S395R;
V59A+A393R+L66R+S340G; V59A+A393R+S340G+S395R;
V59A+A393R+S395R+L66R+S340G; V59A+Y402F+L66R; V59A+Y402F+S340G;
V59A+Y402F+S395R; V59A+Y402F+L66R+S395R; V59A+Y402F+L66R+S340G;
V59A+Y402F+L66R+S395R+S340G; V59A+E408R+L66R; V59A+E408R+S395R;
V59A+E408R+S340G; V59A+E408R+S395R+S340G; V59A+E408R+L66R+S340G;
V59A+E408R+L66R+S395R; V59A+E408R+L66R+S395R+S340G;
V59A+S119P+N313G+L66R;
V59A+S119P+N313G+L66R+S340G; V59A+S119P+N313G+L66R+S395R;
V59A+S119P+N313G+L66R+S395R+S340G; V59A+N313G+A393R+L66R;
V59A+N313G+A393R+L66R+S395R; V59A+N313G+A393R+L66R+S340G;
V59A+N313G+A393R+L66R+S340G+S395R; V59A+A393R+Y402F;
V59A+Y402F+E408R; V59A+S119P+N313G+A393R;
V59A+N313G+A393R+Y402F; V59A+A393R+Y402F+E408R;
V59A+S119P+N313G+A393R+Y402F;
V59A+N313G+A393R+Y402F+E408R;
S119P+N313G; N313G+A393R; A393R+Y402F; Y402F+E408R;
S119P+N313G+A393R; N313G+A393R+Y402F; A393R+Y402F+E408R;
V59A+S119P+N313G+A393R+Y402F; N313G+A393R+Y402F+E408R;
S119P+L66R; V59A+S119P+S340G; S119P+S395R; S119P+L66R+S340G;
S119P+S340G+S395R; S119P+S395R+L66R; S119P+S395R+L66R+S340G;
N313G+L66R; N313G+S340G; N313G+S395R; N313G+L66R+S340G;
N313G+S340G+S395R; N313G+S395R+L66R; N313G+S395R+L66R+S340G;
A393R+L66R; A393R+S340G; A393R+S395R; A393R+L66R+S340G;
A393R+S340G+S395R; A393R+S395R+L66R+S340G;
Y402F+S340G; Y402F+S395R; Y402F+L66R+S395R; Y402F+L66R+S340G;
Y402F+L66R+S395R+S340G; E408R+L66R; E408R+S395R; E408R+S340G;
E408R+S395R+S340G; E408R+L66R+S340G; E408R+L66R+S395R;
E408R+L66R+S395R+S340G; S119P+N313G+L66R; S119P+N313G+L66R+S340G;
S119P+N313G+L66R+S395R; S119P+N313G+L66R+S395R+S340G;
N313G+A393R+L66R; N313G+A393R+L66R+S395R; N313G+A393R+L66R+S340G;
N313G+A393R+ L66R+S340G+S395R; A393R+Y402F;
Y402F+E408R; V59A+S119P+N313G+A393R; N313G+A393R+Y402F;
A393R+Y402F+E408R; S119P+N313G+A393R+Y402F;
N313G+A393R+Y402F+E408R.
V59A+S119P+S340G; S119P+S395R; S119P+S340G; S119P+S340G+S395R;
S119P+S395R; S119P+S395R+S340G; N313G+S340G; N313G+S395R;
N313G+S340G; N313G+S395R; N313G+S395R+S340G; A393R+S340G;
A393R+S395R+S340G; Y402F+S395R; Y402F+S340G; Y402F+S395R+S340G;
E408R+S340G; E408R+S395R; E408R+S395R+S340G; S119P+N313G;
S119P+N313G+S340G; S119P+N313G+S395R; S119P+N313G+S395R+S340G;
N313G+A393R; N313G+A393R+S395R; N313G+A393R+S340G; N313G+A393R+S340G+S395R;
N313G+A393R; V59A+N313G+A393R+Y402F; V59A+S340G; L66R+S340G;
S340G+S395R; S395R+L66R; S395R+L66R+S340G; N313G+L66R;
N313G+L66R+S340G; N313G+L66R+S395R; N313G+L66R+S395R+S340G;
V59A+N313G+A393R; N313G+A393R+Y402F;
S119P+A393R; A393R+Y402F; V59A+S119P+A393R+Y402F;
A393R+Y402F+E408R; S119P+S395R+L66R+S340G; L66R+S340G;
S340G+S395R; S395R+L66R; S395R+L66R+S340G; S119P+L66R;
S119P+L66R+S340G; S119P+L66R+S395R; S119P+L66R+S395R+S340G;
A393R+L66R; A393R+L66R+S395R; A393R+L66R+S340G; A393R+L66R+S340G+S395R;
V59A+S119P+A393R; A393R+Y402F; S119P+A393R+Y402F; A393R+Y402F+E408R;
S119P+N313G; N313G+Y402F; Y402F+E408R; V59A+S119P+N313G+Y402F;
N313G+Y402F+E408R; L66R+S340G; S340G+S395R; S395R+L66R+S340G;
N313G+L66R; N313G+L66R+S395R; N313G+L66R+S340G;
N313G+L66R+S340G+S395R;
V59A+S119P+N313G; N313G+Y402F; Y402F+E408R; S119P+N313G+Y402F;
N313G+Y402F+E408R.
S119P+S340G; S119P+L66R; S119P+L66R+S340G;
N313G+S340G;
N313G+L66R; N313G+L66R+S340G; A393R+S340G;
A393R+L66R+S340G;

Y402F+L66R; Y402F+L66R+S340G; Y402F+L66R+S340G; E408R+S340G;
E408R+L66R; E408R+L66R+S340G;
S119P+N313G+L66R; S119P+N313G+L66R+S340G;
N313G+A393R+L66R;
N313G+A393R+L66R+S340G;
N313G+A393R; A393R+E408R; V59A+S119P+N313G+A393R;
N313G+A393R+E408R;
L66R+S395R; L66R+S340G; L66R+S395R+S340G; N313G+A393R;
A393R+E408R; S119P+N313G+A393R; N313G+A393R+E408R.
A393R+Y402F; N313G+A393R+Y402F; S395R+S340G; L66R+S340G;
L66R+S395R; L66R+S395R+S340G; A393R+Y402F; N313G+A393R+Y402F.
S119P+L66R; V59A+S119P; S119P+S395R; S119P+L66R; S119P+S395R;
S119P+S395R+L66R; N313G+L66R; N313G+S395R; N313G+S395R+L66R;
A393R+L66R; A393R+S395R; A393R+S395R+L66R; Y402F+L66R;
Y402F+L66R+S395R; E408R+S395R; E408R+L66R; E408R+L66R+S395R;
S119P+N313G+L66R; S119P+N313G+L66R+S395R; N313G+A393R+L66R;
N313G+A393R+L66R+S395R;
N9A+S56A+V59A+S119P+A246T+N313G+E342T+A393R+S394R+Y402F+E408R;
S56A+V59A+S119P+A246T+N313G+E342T+A393R+S394R+Y402F+E408R;
V59A+S119P+A246T+N313G+E342T+A393R+S394R+Y402F+E408R;
S119P+A246T+N313G+E342T+A393R+S394R+Y402F+E408R;
A246T+N313G+E342T+A393R+S394R+Y402F+E408R; N313G+E342T+A393R+S394R+Y402F+E408R;
E342T+A393R+S394R+Y402F+E408R;
A393R+S394R+Y402F+E408R; S394R+Y402F+E408R; Y402F+E408R;
V59A+L66R+T72I+S119P+N313G+S340G+S356G+A393R+Y402F+E408R+N427M;
L66R+T72I+S119P+N313G+S340G+S356G+A393R+Y402F+E408R+N427M;
T72I+S119P+N313G+S340G+S356G+A393R+Y402F+E408R+N427M;
S119P+N313G+S340G+S356G+A393R+Y402F+E408R+N427M;
N313G+S340G+S356G+A393R+Y402F+E408R+N427M; S340G+S356G+A393R+Y402F+E408R+N427M;
S356G+A393R+Y402F+E408R+N427M; A393R+Y402F+E408R+N427M;
Y402F+E408R+N427M; E408R+N427M;
I189T+Y223F+F227Y+S119P+Y402F; Y223F+F227Y+S119P+Y402F;
F227Y+S119P+Y402F; S119P+Y402F; I189T+Y223F+F227Y+Y402F;
I189T+Y223F+F227Y; I189T+Y223F; I189T+F227Y; I189T+F227Y+S119P;
I189T+F227Y+Y402F; Y223F+F227Y+Y402F; Y223F+F227Y+S119P.

The invention also relates to a variant of a parent glucoamylase which parent glucoamylase is encoded by a nucleic acid sequence which hybridizes under medium, more preferably high stringency conditions, with the nucleic acid sequence of SEQ ID NO: 1 or its complementary strand.

Improved Thermal Stability

In still another aspect, the invention relates to a variant of a parent glucoamylase with improved thermal stability, in particular in the range from 40-80° C., preferably 63-75° C., in particular at pH 4-5, using maltodextrin as the substrate, said variant comprising one or more mutations in the following positions in the amino acid sequence shown in SEQ ID NO: 2: 59, 66, 72, 119, 189, 223, 227, 313, 340, 342, 352, 379, 386, 393, 395, 402, 408, 416, 425, 427, 444, 486, 490, 494, or in a corresponding position in a homologous glucoamylase which displays at least 60% homology with the amino acid sequences shown in SEQ ID NO: 2.

Specific substitutions contemplated to give improved thermal stability including: V59A, L66V/R, T72I, S119P, I189T, Y223F, F227Y, N313G, S340G, E342A, R, D, N, C, Q, G, H, I, L, K, M, F, P, S, T, W, Y, V, preferably E342T, K352R, S356G, T379A, S386K, N, R, P, A393R, S395R, Y402F, E408R, T416A, R, D, N, C, Q, G, H, I, L, K, M, F, P, S, E, W, Y, V, preferably T416H, A425T, N427S/M, S444G, S486G, T490A, T494P/A.

Specific combinations of mutations include:
E408R+A425T+S465P+T494A,
A425T+E408R+S386K+A495T,
T379A+T2E+S386K+A393R,
S386N+E408R,
L66V+T2R+S394P+Y402F+RL(N-terminal extension),
S386R+T2R+A393R.
N427S+S486G+A1V+L66R+Y402F,
N427M+S44G+V470M+T2K+S30P,
T490A+V59A++A393R+PLASD (N-terminal extension)

All of the variant listed in the section "Glucoamylase variants of the invention" are contemplated to have improved thermostability. Examples 2 and 4 show this for selected variants of the invention.

Increased Specific Activity

In still another aspect, the invention relates to a variant of a parent glucoamylase with improved specific activity, said variant comprising one or more mutations in the following positions in the amino acid sequence shown in SEQ ID NO: 2: 59, 66, 72, 119, 189, 223, 227, 313, 340, 342, 352, 379, 386, 393, 395, 402, 408, 416, 425, 427, 444, 486, 490, 494, preferably 189, 223, 227 or in a corresponding position in a homologous glucoamylase which displays at least 60% homology with the amino acid sequences shown in SEQ ID NO: 2.

Specific mutations contemplated to give increased specific activity include: V59A, L66V/R, T72I, S119P, I189T, Y223F, F227Y, N313G, S340G, K352R, S356G, T379A, S386K, N, R, P, A393R, S395R, Y402F, E408R, T416A, R, D, N, C, Q, G, H, I, L, K, M, F, P, S, E, W, Y, V preferably T416H, A425T, N427S/M, S444G S486G, T490A, T494P/A, preferably I189T, Y223F, F227Y.

Specific combinations of mutations include:
I189T+Y223F+F227Y+S119P+Y402F;
Y223F+F227Y+S119P+Y402F; F227Y+S119P+Y402F; S119P+Y402F;
I189T+Y223F+F227Y+Y402F; I189T+Y223F+F227Y;
I189T+Y223F;
I189T+F227Y; I189T+F227Y+S119P; I189T+F227Y+Y402F;
Y223F+F227Y+Y402F; Y223F+F227Y+S119P.

All of the variant listed in the section "Glucoamylase variants of the invention" are contemplated to have increased specific activity. Example 3 shows this for a selected variant of the invention.

Homology (Identity)

The homology referred to above of the parent glucoamylase is determined as the degree of identity between two protein sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443-453). Using GAP with the following settings for polypeptide sequence comparison: GAP creation penalty of 3.0 and GAP extension penalty of 0.1, the mature part of a polypeptide encoded by an analogous DNA sequence of the invention exhibits a degree of identity preferably of at least 80%, at least 90%, more preferably at least 95%, more preferably at least 97%, and most preferably at least 99% with the mature part of the amino acid sequence shown in SEQ ID NO: 2.

In an embodiment the parent glucoamylase is the *Aspergillus niger* G1 glucoamylase (Boel et al. (1984), EMBO J. 3 (5), p. 1097-1102 (SEQ ID NO: 13). The parent glucoamylase may be a truncated glucoamylase, e.g., the *A. niger* G2 glucoamylase (SEQ ID NO: 2).

Preferably, the parent glucoamylase comprises the amino acid sequences of SEQ ID NO: 2; or allelic variants thereof; or a fragment thereof that has glucoamylase activity.

A fragment of SEQ ID NO: 2 is a polypeptide which has one or more amino acids deleted from the amino and/or carboxyl terminus of this amino acid sequence. For instance, the AMG G2 (SEQ ID NO: 2) is a fragment of the *Aspergillus niger* G1 glucoamylase (Boel et al. (1984), EMBO J. 3 (5), p. 1097-1102) having glucoamylase activity. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of homologous parent glucoamylases may differ from the amino acid sequence of SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the isolated parent glucoamylase is encoded by a nucleic acid sequence which hybridises under very low stringency conditions, preferably low stringency conditions, more preferably medium stringency conditions, more preferably medium-high stringency conditions, even more preferably high stringency conditions, and most preferably very high stringency conditions with a nucleic acid probe which hybridises under the same conditions with (i) the nucleic acid sequence of SEQ ID NO: 1, (ii) the cDNA sequence of SEQ ID NO:1, (iii) a sub-sequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The sub-sequence of SEQ ID NO: 1 may be at least 100 nucleotides or preferably at least 200 nucleotides. Moreover, the sub-sequence may encode a polypeptide fragment, which has glucoamylase activity. The parent polypeptides may also be allelic variants or fragments of the polypeptides that have glucoamylase activity.

The nucleic acid sequence of SEQ ID NO: 1 or a subsequence thereof, as well as the amino acid sequence of SEQ ID NO: 2, or a fragment thereof, may be used to design a nucleic acid probe to identify and clone DNA encoding polypeptides having glucoamylase activity, from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA, which hybridizes with the probes described above and which encodes a polypeptide having glucoamylase. Genomic or other DNA from such other organisms may be separated by agarose or polyacrylamide gel electrophoresis, or other separation techniques. DNA from the libraries or the separated DNA may be transferred to and immobilised on nitrocellulose or other suitable carrier material. In order to identify a clone or DNA which is homologous with SEQ ID NO: 1, or sub-sequences thereof, the carrier material is used in a Southern blot. For purposes of the present invention, hybridisation indicates that the nucleic acid sequence hybridises to a nucleic acid probe corresponding to the nucleic acid sequence shown in SEQ ID NO: 1 its complementary strand, or a sub-sequence thereof, under very low to very high stringency conditions. Molecules to which the nucleic acid probe hybridises under these conditions are detected using X-ray film.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridisation, and washing post-hybridisation at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes, which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridising a DNA under very low, low, medium, medium-high, high, or very high stringency conditions with the sequence of SEQ ID NO:1, or its complementary strand, or a sub-sequence thereof; and (b) isolating the nucleic acid sequence. The sub-sequence is preferably a sequence of at least 100 nucleotides such as a sequence, which encodes a polypeptide fragment, which has glucoamylase activity.

Contemplated parent glucoamylases have at least 20%, preferably at least 40%, more preferably at least 60%, even more preferably at least 80%, even more preferably at least 90%, and most preferably at least 100% of the glucoamylase activity of the mature glucoamylase of SEQ ID NO: 2.

Cloning a DNA Sequence Encoding a Parent Glucoamylase

The DNA sequence encoding a parent glucoamylase may be isolated from any cell or microorganism producing the glucoamylase in question, using various methods well known in the art. First, a genomic DNA and/or cDNA library should be constructed using chromosomal DNA or messenger RNA from the organism that produces the glucoamylase to be studied. Then, if the amino acid sequence of the glucoamylase is known, labeled oligonucleotide probes may be synthesized and used to identify glucoamylase-encoding clones from a genomic library prepared from the organism in question. Alternatively, a labelled oligonucleotide probe containing sequences homologous to another known glucoamylase gene could be used as a probe to identify glucoamylase-encoding clones, using hybridization and washing conditions of very low to very high stringency. This is described above.

Yet another method for identifying glucoamylase-encoding clones would involve inserting fragments of genomic DNA into an expression vector, such as a plasmid, transforming glucoamylase-negative bacteria with the resulting genomic DNA library, and then plating the transformed bacteria onto agar containing a substrate for glucoamylase (i.e., maltose), thereby allowing clones expressing the glucoamylase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487-491.

Site-Directed Mutagenesis

Once a glucoamylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the glucoamylase-encoding sequence, is created in a vector carrying the glucoamylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646-639. U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into glucoamylase-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Further, Sierks. et al., (1989) "Site-directed mutagenesis at the active site Trp120 of *Aspergillus awamori* glucoamylase. Protein Eng., 2, 621-625; Sierks et al., (1990), "Determination of *Aspergillus awamori* glucoamylase catalytic mechanism by site-directed mutagenesis at active site Asp176, Glu179, and Glu10". Protein Eng. vol. 3, 193-198; also describes site-directed mutagenesis in an *Aspergillus* glucoamylase.

Localized Random Mutagenesis

The random mutagenesis may be advantageously localized to a part of the parent glucoamylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative methods for providing variants of the invention include gene shuffling, e.g., as described in WO 95/22625 (from Affymax Technologies N.V.) or in WO 96/00343 (from Novo Nordisk A/S).

Expression of Glucoamylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a glucoamylase variant of the invention may be any vector, which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell.

Examples of suitable promoters for directing the transcription of the DNA sequence encoding a glucoamylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xy1A and xy1B genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual,* 2nd Ed., Cold Spring Harbor, 1989).

Host Cells

The cell of the invention, either comprising a DNA construct or an expression vector of the invention as defined above, is advantageously used as a host cell in the recombinant production of a glucoamylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E. coli.* The transformation of the bacteria may, for instance, be effected by protoplast transformation or by using competent cells in a manner known per se.

The yeast organism may favorably be selected from a species of *Saccharomyces* or *Schizosaccharomyces,* e.g., *Saccharomyces cerevisiae.*

The host cell may also be a filamentous fungus, e.g., a strain belonging to a species of *Aspergillus,* most preferably *Aspergillus oryzae* or *Aspergillus niger,* or a strain of *Fusarium,* such as a strain of *Fusarium oxysporium, Fusarium graminearum* (in the perfect state named *Gibberella zeae,* previously *Sphaeria zeae,* synonym with *Gibberella roseum* and *Gibberella roseum* f. sp. *cerealis*), or *Fusarium sulphureum* (in the prefect state named *Gibberella puricaris,* synonym with *Fusarium trichothecioides, Fusarium bactridioides, Fusarium sambucium, Fusarium roseum,* and *Fusarium roseum var. graminearum*), *Fusarium cerealis* (synonym with *Fusarium crokkwellnse*), or *Fusarium venenatum.*

In a preferred embodiment of the invention the host cell is a protease deficient or protease minus strain.

This may for instance be the protease deficient strain *Aspergillus oryzae* JaL 125 having the alkaline protease gene named "alp" deleted. This strain is described in WO 97/35956 (Novo Nordisk), or EP patent no. 429,490.

Filamentous fungi cells may be transformed by a process involving protoplast formation and transformation of the protoplasts followed by regeneration of the cell wall in a manner known per se. The use of *Aspergillus* as a host micro-organism is described in EP 238,023 (Novo Nordisk A/S), the contents of which are hereby incorporated by reference.

Method of Producing Glucoamylase Variants

In a yet further aspect, the present invention relates to a method of producing a glucoamylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the glucoamylase variant of the invention. Suitable media are available from commercial suppliers or may be prepared according to published recipes (e.g. as described in catalogues of the American Type Culture Collection).

The glucoamylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Starch Conversion

The present invention provides a method of using glucoamylase variants of the invention for producing glucose and the like from starch. Generally, the method includes the steps of partially hydrolyzing precursor starch in the presence of alpha-amylase and then further hydrolyzing the release of D-glucose from the non-reducing ends of the starch or related oligo- and polysaccharide molecules in the presence of glucoamylase by cleaving alpha-(1→4) and alpha-(1→6) glucosidic bonds.

The partial hydrolysis of the precursor starch utilizing α-amylase provides an initial breakdown of the starch molecules by hydrolyzing internal alpha-(1→4)-linkages. In commercial applications, the initial hydrolysis using alpha-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30° and 60° C. Preferably the temperature of the substrate liquid is dropped to between 55° C. and 60° C. The pH of the solution is dropped from 6 to 6.5 to a range between 3 and 5.5. Preferably, the pH of the solution is 4 to 4.5. The glucoamylase is added to the solution and the reaction is carried out for 24-72 hours, preferably 36-48 hours.

By using a thermostable glucoamylase variant of the invention saccharification processes may be carried out at a higher temperature than traditional batch saccharification processes. According to the invention saccharification may be carried out at temperatures in the range from above 60-80° C., preferably 63-75° C. This applied both for traditional batch processes (described above) and for continuous saccharification processes.

Actually, continuous saccharification processes including one or more membrane separation steps, i.e., filtration steps, must be carried out at temperatures of above 60° C. to be able to maintain a reasonably high flux over the membrane. Therefore, the thermostable variants of the invention provides the possibility of carrying out large scale continuous saccharification processes at a fair price within and period of time acceptable for industrial saccharification processes. According to the invention the saccharification time may even be shortened.

The activity of the glucoamylase variant (e.g., AMG variant) of the invention is generally substantially higher at temperatures between 60° C.-80° C. than at the traditionally used temperature between 30-60° C. Therefore, by increasing the temperature at which the glucoamylase operates the saccharification process may be carried out within a shorter period of time.

Further, by improving the thermal stability the $T_{1/2}$ (half-time, as defined in the "Materials and Methods" section) is improved. As the thermal stability of the glucoamylase variants of the invention is improved a minor amount of glucoamylase need to be added to replace the glucoamylase being inactivated during the saccharification process. More glucoamylase is maintained active during saccharification process according to the present invention. Furthermore, the risk of microbial contamination is also reduced when carrying the saccharification process at temperature above 63° C.

An example of saccharification process wherein the glucoamylase variants of the invention may be used include the processes described in JP 3-224493; JP 1-191693; JP 62-272987; and EP 452,238.

The glucoamylase variant(s) of the invention may be used in the present inventive process in combination with an enzyme that hydrolyzes only alpha-(1→6)-glucosidic bonds in molecules with at least four glucosyl residues. Preferentially, the glucoamylase variant of the invention can be used in combination with pullulanase or isoamylase. The use of isoamylase and pullulanase for debranching, the molecular properties of the enzymes, and the potential use of the enzymes with glucoamylase is set forth in G. M. A. van Beynum et al., Starch Conversion Technology, Marcel Dekker, N.Y., 1985, 101-142.

In a further aspect the invention relates to the use of a glucoamylase variant of the invention in a starch conversion process.

Further, the glucoamylase variant of the invention may be used in a continuous starch conversion process including a continuous saccharification step.

The glucoamylase variants of the invention may also be used in immobilised form. This is suitable and often used for producing maltodextrins or glucose syrups or specialty syrups, such as maltose syrups, and further for the raffinate stream of oligosaccharides in connection with the production of fructose syrups.

According to the invention the AMG variant of the invention may also be used for producing ethanol, e.g., for fuel or drinking. A contemplated method is described in U.S. Pat. No. 5,231,017.

Materials & Methods

Enzymes:

AMG G1: *Aspergillus niger* glucoamylase G1 disclosed in Boel et al., (1984), EMBO J. 3 (5), 1097-1102, (SEQ ID NO: 13), available from Novo Nordisk.

AMG G2: Truncated *Aspergillus niger* glucoamylase G1 shown in SEQ ID NO: 2, available from Novo Nordisk)

Solutions:

Buffer: 0.05M sodium acetate (6.8 g in 1 l milli-Q-water), pH 4.5

Stop solution: 0.4M NaOH

GOD-perid, 124036, Boehringer Mannheim

Substrate:

Maltose: 29 mM (1 g maltose in 100 ml 50 mM sodium acetate, pH 4.5) (Sigma)

Maltoheptaose: 10 mM, 115 mg/10 ml (Sigma)

Host Cell:

*A. oryzae* JaL 125: *Aspergillus oryzae* IFO 4177 available from Institute for Fermention, Osaka; 17-25 Juso Hammachi 2-Chome Yodogawa-ku, Osaka, Japan, having the alkaline protease gene named "alp" (described by Murakami K et al., (1991), Agric. Biol. Chem. 55, p. 2807-2811) deleted by a one step gene replacement method (described by G. May in "Applied Molecular Genetics of Filamentous Fungi" (1992), p. 1-25. Eds. J. R. Kinghorn and G. Turner; Blackie Academic and Professional), using the *A. oryzae* pyrG gene as marker. Strain JaL 125 is further disclosed in WO 97/35956 (Novo Nordisk).

Micro-Organisms:

Strain: *Saccharomyces cerevisiae* YNG318: MATαleu2-Δ2 ura3-52 his4-539 pep4-Δ1 [cir+]

Plasmids:

pCAMG91: see FIG. 1. Plasmid comprising the *Aspergillus niger* G1 glucoamylase (AMG G1). The construction of pCAMG91 is described in Boel et al. (1984), EMBO J. 3 (7) p. 1581-1585.

pMT838: Plasmid encoding the truncated *Aspergillus niger* glucoamylase G2 (SEQ ID NO: 2).

pJSO026 (*S. cerevisiae* expression plasmid)(J. S. Okkels, (1996) "A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences) More specifically, the expression plasmid pJSO37, is derived from pYES 2.0 by replacing the inducible GAL1-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419-434), and deleting a part of the URA3 promoter.

Methods:

Transformation of *Saccharomyces cerevisiae* YNG318

The DNA fragments and the opened vectors are mixed and transformed into the yeast *Saccharomyces cerevisiae* YNG318 by standard methods.

Determining Specific Activity As $k_{cat}$ (sec.$^{-1}$)

750 microL substrate (1% maltose, 50 mM Sodium acetate, pH 4.3) is incubated 5 minutes at selected temperature, such as 37° C. or 60° C.

50 microL enzyme diluted in sodium acetate is added. Aliquots of 100 microL are removed after 0, 3, 6, 9 and 12 minutes and transferred to 100 microL 0.4 M Sodium hydroxide to stop the reaction. A blank is included.

20 microL is transferred to a Micro titre plates and 200 microL GOD-Perid solution is added. Absorbance is measured at 650 nm after 30 minutes incubation at room temperature.

Glucose is used as standard and the specific activity is calculated as $k_{cat}$ (sec.$^{-1}$).

Determination of AGU Activity and as AGU/mg

One Novo Amyloglucosidase Unit (AGU) is defined as the amount of enzyme, which hydrolyzes 1 micromole maltose per minute at 37° C. and pH 4.3. A detailed description of the analytical method (AEL-SM-0131) is available on request from Novo Nordisk.

The activity is determined as AGU/ml by a method modified after (AEL-SM-0131) using the Glucose GOD-Perid kit from Boehringer Mannheim, 124036. Standard: AMG-standard, batch 7-1195, 195 AGU/ml.

375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution is added. After 30 minutes at room temperature, the absorbance is measured at 650 nm and the activity calculated in AGU/ml from the AMG-standard.

The specific activity in AGU/mg is then calculated from the activity (AGU/ml) divided with the protein concentration (mg/ml).

Transformation of *Aspergillus* (General Procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5-2.5 hours at 37 C until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the $MgSO_4$ cushion. 2 volumes of STC (1.2 M sorbitol, 10 mM Tris-HCl, pH 7.5, 10 mM $CaCl_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2-1 ml of STC.

100 µl of protoplast suspension are mixed with 5-25 µg of p3SR2 (an *A. nidulans* amdS gene carrying plasmid described in Hynes et al., Mol. and Cel. Biol., Vol. 3, No. 8, 1430-1439, August 1983) in 10 µl of STC. The mixture is left at room temperature for 25 min. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2 M sorbitol. After one more sedimentation the protoplasts are spread on minimal plates (Cove, (1966), Biochem. Biophys. Acta 113, 51-56) containing 1.0 M sucrose, pH 7.0, 10 mM acetamide as nitrogen source and 20 mM CsCl to inhibit background growth. After incubation for 4-7 days at 37 C spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration.

Purification

The culture broth is filtrated and added ammoniumsulphate (AMS) to a concentration of 1.7 M AMS and pH is adjusted to pH 5. Precipitated material is removed by centrifugation and the solution containing glucoamylase activity is applied on a Toyo Pearl Butyl column previously equilibrated in 1.7 M AMS, 20 mM sodium acetate, pH 5. Unbound material is washed out with the equilibration buffer. Bound proteins are eluted with 10 mM sodium acetate, pH 4.5 using a linear gradient from 1.7-0 M AMS over 10 column volumes. Glucoamylase containing fractions are collected and dialysed against 20 mM sodium acetate, pH 4.5. The solution was then applied on a Q sepharose column, previously equilibrated in 10 mM Piperazin, Sigma, pH 5.5. Unbound material is washed out with the equilibration buffer. Bound proteins are eluted with a linear gradient of 0-0.3 M Sodium chloride in 10 mM Piperazin, pH 5.5 over 10 column volumes. Glucoamylase containing fractions are collected and the purity was confirmed by SDS-PAGE.

$T_{1/2}$ (Half-Life) Method I

The thermal stability of variants is determined as $T_{1/2}$ using the following method: 950 microliter 50 mM sodium acetate buffer (pH 4.3) (NaOAc) is incubated for 5 minutes at 68° C., 70° C. or 75 C. 50 microliter enzyme in buffer (4 AGU/ml) is added. 2×40 microliter samples are taken at, e.g., 0, 5, 10, 20, 30 and 40 minutes and chilled on ice. The activity (AGU/ml) measured before incubation (0 minutes) is used as reference (100%). The decline in stability (in percent) is calculated as a function of the incubation time. The % residual glucoamylase activity is determined at different times. $T_{1/2}$ is the period of time until which the % relative activity is decreased to 50%.

$T_{1/2}$ (Half-Life) (Method II)

The $T_{1/2}$ is measured by incubating the enzyme (ca 0.2 AGU/ml) in question in 30% glucose, 50 mM Sodium acetate at pH 4.5 at the temperature in question (e.g., 70° C.). Samples are withdrawn at set time intervals and chilled on ice and residual enzyme activity measured by the pNPG method (as described below).

The % residual glucoamylase activity is determined at different times. $T_{1/2}$ is the period of time until which the % relative activity is decreased to 50%.

Residual Enzyme Activity (pNPG Method)

pNPG Reagent:

0.2 g pNPG (p-nitrophenylglucopyranoside) is dissolved in 0.1 M acetate buffer (pH 4.3) and made up to 100 ml.

Borate Solution:

3.8 g $Na_2B_4O_7.10\ H_2O$ is dissolved in Milli-Q water and made up to 100 ml.

25 microL samples are added 50 microL substrate and incubated 2 hr at 50° C. The reaction is stopped by adding 150 microL ml borate solution. The optical density is measured at 405 nm, and the residual activity calculated.

Construction of pAMGY

The pAMGY vector was constructed as follows: The lipase gene in pJSO026 was replaced by the AMG gene, which was PCR amplified with the forward primer; FG2: 5'-CAT CCC CAG GAT CCT TAC TCA GCA ATG-3' (SEQ ID NO: 10) and the reverse primer: RG2: 5'-CTC AAA CGA CTC ACC AGC CTC TAG AGT-3' (SEQ ID NO: 11) using the template plasmid pLAC103 containing the AMG gene. The pJSO026 plasmid was digested with XbaI and SmaI at 37° C. for 2 hours and the PCR amplicon was blunt ended using the Klenow fragment and then digested with XbaI. The vector fragment and the PCR amplicon were ligated and transformed into E. coli by electrotransformation. The resulting vector is designated pAMGY.

Construction of pLaC103

The A. niger AMGII cDNA clone (Boel et al., (1984), supra) is used as source for the construction of pLaC103 aimed at S. cerevisiae expression of the GII form of AMG.

The construction takes place in several steps, out lined below.

pT7-212 (EP37856/U.S. Pat. No. 5,162,498) is cleaved with XbaI, blunt-ended with Klenow DNA polymerase and dNTP. After cleavage with EcoRI the resulting vector fragment is purified from an agarose gel-electrophoresis and ligated with the 2.05 kb EcoR1-EcoRV fragment of pBoe153, thereby recreating the XbaI site in the EcoRV end of the AMG encoding fragment in the resulting plasmid pG2x.

In order to remove DNA upstream of the AMG cds, and furnish the AMG encoding DNA with an appropriate restriction endonuclease recognition site, the following construct was made:

The 930 bp EcoRI-PstI fragment of p53 was isolated and subjected to AluI cleavage, the resulting 771 bp Alu-PstI fragment was ligated into pBR322 with blunt-ended EcoRI site (see above) and cleaved with PstI In the resulting plasmid pBR-AMG', the EcoRI site was recreated just 34 bp from the initiation codon of the AMG cds.

From pBR-AMG' the 775 bp EcoRI-PstI fragment was isolated and joined with the 1151 bp PstI-XbaI fragment from pG2x in a ligation reaction including the XbaI-EcoRI vector fragment of pT7-212.

The resulting plasmid pT7GII was submitted to a BamHI cleavage in presence of alkaline phosphatase followed by partial SphI cleavage after inactivation of the phosphatase. From this reaction was the 2489 bp SphI-BamHI fragment, encompassing the S.c. TPI promoter linked to the AMGII cds. The above fragment together with the 1052 bp BamHI fragment of pT7GII was ligated with the alkaline phosphatase treated vector fragment of pMT743 (EP37856/U.S. Pat. No. 5,162,498), resulting from SphI-BamHI digestion. The resulting plasmid is pLaC103.

Screening for Thermostable AMG Variants

The libraries are screened in the thermostable filter assay described below.

Filter Assay for Thermostability

Yeast libraries are plated on a sandwich of cellulose acetate (OE 67, Schleicher & Schuell, Dassel, Germany)—and nitrocellulose filters (Protran-Ba 85, Schleicher & Schuell, Dassel, Germany) on SCFuraagar plates with 100 μg/ml ampicillin at 30° C. for at least 72 hrs. The colonies are replica plated to PVDF filters (Immobilon-P, Millipore, Bedford) activated with methanol for 1 min or alternatively a Protran filter (no activation) and subsequently washed in 0.1 M NaAc and then incubated at room temperature for 2 hours. Colonies are washed from PVDF/Protran filters with tap water. Each filter sandwiches and PVDF/Protran filters are specifically marked with a needle before incubation in order to be able to localise positive variants on the filters after the screening. The PVDF filters with bound variants are transferred to a container with 0.1 M NaAc, pH 4.5 and incubated at 47° C. or alternatively 67-69° C. in case of Protran filters for 15 minutes. The sandwich of cellulose acetate and nitrocellulose filters on SC ura-agar plates are stored at room temperature until use. After incubation, the residual activities are detected on plates containing 5% maltose, 1% agarose, 50 mM NaAc, pH 4.5. The assay plates with PVDF filters are marked the same way as the filter sandwiches and incubated for 2 hrs. at 50° C. After removal of the PVDF filters, the assay plates are stained with Glucose GOD perid (Boehringer Mannheim GmbH, Germany). Variants with residual activity are detected on assay plates as dark green spots on white background. The improved variants are located on the storage plates. Improved variants are rescreened twice under the same conditions as the first screen.

General Method for Random Mutagenesis by Use of the Dope Program

The random mutagenesis may be carried out by the following steps:

1. Select regions of interest for modification in the parent enzyme,

2. Decide on mutation sites and non-mutated sites in the selected region,

3. Decide on which kind of mutations should be carried out, e.g., with respect to the desired stability and/or performance of the variant to be constructed, 4. Select structurally reasonable mutations, 5. Adjust the residues selected by step 3 with regard to step 4.

6. Analyze by use of a suitable dope algorithm the nucleotide distribution.

7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted 8. Make primers 9. Perform random mutagenesis by use of the primers 10. Select resulting glucoamylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

EXAMPLES

Example 1

Construction of AMG G2 Variants

Site-Directed Mutagenesis

For the construction of variants of a AMG G2 enzyme (SEQ ID NO: 2) the commercial kit, Chameleon double-stranded, site-directed mutagenesis kit was used according to the manufacturer's instructions.

The gene encoding the AMG G2 enzyme in question is located on pMT838 prepared by deleting the DNA between G2 nt. 1362 and G2 nt. 1530 in plasmid pCAMG91 (see FIG. 1) comprising the AMG G1 form.

In accordance with the manufacturer's instructions the ScaI site of the Ampicillin gene of pMT838 was changed to a MluI site by use of the following primer:
7258: 5'p gaa tga ctt ggt tga cgc gtc acc agt cac 3' (SEQ ID NO: 3).
(Thus changing the ScaI site found in the ampicillin resistance gene and used for cutting to a MluI site). The pMT838 vector comprising the AMG gene in question was then used as a template for DNA polymerase and oligo 7258 (SEQ ID NO: 3) and 21401 (SEQ ID NO: 4).

Primer no. 21401 (SEQ ID NO: 4) was used as the selection primer.
21401: 5'p gg gga tca tga tag gac tag cca tat taa tga agg gca tat acc acg cct tgg acc tgc gtt ata gcc 3'
(Changes the ScaI Site Found in the AMG Gene without Changing the Amino Acid Sequence).

The desired mutation (e.g., the introduction of a cystein residue) is introduced into the AMG gene in question by addition of an appropriate oligos comprising the desired mutation.

The primer 107581 was used to introduce T12P
107581: 5' pgc aac gaa gcg ccc gtg gct cgt ac 3' (SEQ ID NO: 5)

The mutations are verified by sequencing the whole gene. The plasmid was transformed into A. oryzae using the method described above in the "Materials and Methods" section. The variant was fermented and purified as described above in the "Materials & Methods" section.

Example 2

Construction, by Localized Random, Doped Mutagenesis, of A. niger AMG Variants Having Improved Thermostability Compared to the Parent Enzyme To improve the thermostability of the A. niger AMG random mutagenesis in pre-selected region was performed.
Residue:
Region: L19-G35
Region: A353-V374

The DOPE software (see Materials and Methods) was used to determine spiked codons for each suggested change in the above regions minimizing the amount of stop codons (see table 1). The exact distribution of nucleotides was calculated in the three positions of the codon to give the suggested population of amino acid changes. The doped regions were doped specifically in the indicated positions to have a high chance of getting the desired residues, but still allow other possibilities.

The first column is the amino acid to be mutated, the second column is the percentage of wild type and the third column defined the new amino acid(s).

TABLE 1

| Doping in L19-G35 | | |
|---|---|---|
| L19 | 90% | N |
| N20 | 95% | T |
| N21 | Constant | |
| I22 | Constant | |
| G23 | 95% | A |
| A24 | 90% | S, T |
| D25 | 93% | S, T, R |
| G26 | 95% | A |
| A27 | 90% | S, T |
| W28 | <80% | R, Y |
| V29 | Constant | |
| S30 | 93% | T, N |
| G31 | 95% | A |
| A32 | 95% | V |
| D33 | 80% | R, K, H |
| S34 | 90% | N |
| G35 | Constant | |

The resulting doped oligonucleotide strand is shown in table 2 as sense strand: with the primer sequence, the wild type nucleotide sequence, the parent amino acid sequence and the distribution of nucleotides for each doped position.

TABLE 2

| Position: | 19 | 20 | 21 | 22 | 23 | 24 | 25 | 26 | 27 | 28 |
|---|---|---|---|---|---|---|---|---|---|---|
| A.a. seq.: | L | N | N | I | G | A | D | G | A | W |
| primer: | 12T | A3T | AAC | ATC | G4G | 5CG | 67C | G4T | 8CT | 91010 |
| wt. seq.: | CTG | AAT | AAC | ATC | GGG | GCG | GAC | GGT | GCT | TGG |

TABLE 2-continued

| Pos. (cont.): | 29 | 30 | 31 | 32 | 33 | 34 | 35 |
|---|---|---|---|---|---|---|---|
| A.a. (cont.): | V | S | G | A | D | S | G (SEQ ID NO: 2) |
| primer: | GTG | 1112C | G4C | G13G | 141516 | 1718T | GGC (SEQ ID NO: 14) |
| Wt seq.: | GTG | TCG | GGC | GCG | GAC | TCT | GGC (SEQ ID NO: 1) |

Distribution of nucleotides for each doped position.

1: A10, C90
2: A6, T94
3: A95, C5
4: G95, C5
5: G91, A3, T3, C3
6: G95, A3, C2
7: G3, A95, C2
8: G92, A4, T4
9: A3, T97
10: G95, T5
11: G3, A97
12: G95, A2, C3
13: T5, C95
14: G88, A8, C4
15: G7, A93
16: G4, C96
17: G4, A96
18: G95, A2, C3

Forward primer (SEQ ID NO: 6):
FANGII '5-C GAA GCG ACC GTG GCT CGT ACT GCC ATC 12T A3T AAC ATC G4G
5CG 67C G4T 8CT 91010 GTG 1112C G4C G13G 141516 1718T GGC ATT GTC GTT
GCT AGT CCC AGC ACG GAT AAC-3'

Reverse primer (SEQ ID NO: 7):
RAMG1: 5'-GAT GGC AGT ACG AGC CAC GGT CGC TTC G-3'

TABLE 3

Doping in region A353-V374:

| A353 | <80% | D, E, Q, N, Y |
| L354 | 90% | Q, E |
| Y355 | 90% | N, Q |
| S356 | 90% | T, D, N |
| G357 | 80% | P, A, S, T |
| A358 | 93% | S |
| A359 | 90% | S, T, N |
| T360 | 90% | R, K |
| G361 | 85% | A, S, T |
| T362 | 90% | S |
| Y363 | Constant | |
| S364 | 93% | D |
| S365 | 93% | N, Q, K |
| S366 | 93% | P, D |
| S367 | Constant | |
| S368 | 93% | D, N, T |
| T369 | 93% | Q, E |
| Y370 | Constant | |
| S371 | 93% | N |
| S372 | 93% | N, T |
| I373 | Constant | |
| V374 | 93% | N, Y, H |

The resulting doped oligonucleotide strand is shown in table 4 as sense strand: with the primer sequence, wild type nucleotide sequence, the parent amino acid sequence and the distribution of nucleotides for each doped position.

TABLE 4

| Position: | 353 | 354 | 355 | 356 | 357 | 358 | 359 | 360 | 361 | 362 |
|---|---|---|---|---|---|---|---|---|---|---|
| A.a. seq.: | A | L | Y | S | D | A | A | T | G | T |
| primer: | 123 | 45A | 6AC | 78C | 910T | 11CT | 1213T | 1415A | 1617C | 18CC |
| Wt. seq.: | GCA | CTG | TAC | AGC | GAT | GCT | GCT | ACT | GGC | ACC |

| Pos. (cont.): | 363 | 364 | 365 | 366 | 367 | 368 | 369 | 370 |
|---|---|---|---|---|---|---|---|---|
| A.a. seq. (cont.): | Y | S | S | S | S | S | T | Y |
| primer (cont.): | TAC | 1920T | A2122 | 2324C | AGT | 1425C | 2627G | T28T |
| wt. Seq. (cont.): | TAC | TCT | TCG | TCC | AGT | TCG | ACT | TAT |

TABLE 4-continued

| Pos. (cont.): | 371 | 372 | 373 | 374 |
|---|---|---|---|---|
| A.a. pos. (cont.): | S | S | I | V (SEQ ID NO: 2) |
| primer (cont.) | A16T | 2930T | ATT | 313233 (SEQ ID NO: 15) |
| wt. Seq. (cont.): | AGT | AGC | ATT | GTA (SEQ ID NO: 1) |

Distribution of nucleotides for each doped position.

```
 1: G91, A3, T3, C3
 2: A13, C87
 3: A40, T60
 4: G3, A3, C94
 5: A6, T94
 6: G4, A4, T92
 7: G2, A96, C2
 8: G93, A3.5, C3.5
 9: G87, A8, C5
10: A84, C16
11: G93, T7
12: G92, A5, T3
13: A3, C97
14: G3, A97
15: G2, A2, T4, C92
16: G93, A7
17: G93, C7
18: A90, T10
19: G4, A96
20: G95, A5
21: G96, A4
22: G3, C97
23: G2, A1, T95, C2
24: A3, C97
25: G95, A3, C2
26: G2, A96, C2
27: A5, C95
28: A95, T5
29: G2, A98
30: G94, A4, C2
31: G94, A3, T1, C2
32: A4, T96
33: A20, C80

Primer: FAMGIV (SEQ ID NO: 8)
5'-GTG TCG CTG GAC TTC TTC AAG 123 45A 6AC 78C 910T 11CT
1213T 1415A 1617C 18CC TAC 1920T A2122 2324C AGT 1425C 2627G
T28T A16T 2930C ATT 313233 GAT GCC GTG AAG ACT TTC GCC GA-3'

Primer RAMGVI (SEQ ID NO: 9)
5'-ctt gaa gaa gtc cag cga cac-3'
```

Random Mutagenesis

The spiked oligonucleotides apparent from Table 2 and 3 (which by a common term is designated FAMG) and reverse primers RAMG for the L19-G35 region and specific SEQ ID NO: 2 primers covering the N-terminal (FG2: 5'-CAT CCC CAG GAT CCT TAC TCA GCA ATG-3' (SEQ ID NO: 10) and C-terminal (RG2: 5'-CTC AAA CGA CTC ACC AGC CTC TAG AGT (SEQ ID NO: 11) are used to generate PCR-library-fragments by the overlap extension method (Horton et al., Gene, 77 (1989), pp. 61-68) with an overlap of 21 base pairs. Plasmid pAMGY is template for the Polymerase Chain Reaction. The PCR fragments are cloned by homologous recombination in the *E. coli*/yeast shuttle vector pAMGY (see Materials and Methods).

Screening

The library was screened in the thermostability filter assays using a Protran filter and incubating at 67-69° C. as described in the "Material & Methods" section above Example 2

Thermostability at 68° C.

AMG G2 variants were constructed using the approach described in Example 1.

The thermostability was determined as T½ using Method I at 68° C. as described in the "Materials & Methods" section and compared to the wild-type *A. niger* AMG G2 under the same conditions.

| Enzyme | T½ |
|---|---|
| AMG G2 (wild type) | 8.5 |
| T72I + A246T | 11.3 |
| A495P | 11.0 |
| A425T + S465P + E408R + A495T | 8.6 |
| T379A + S386K + A393R + T2E | 18.4 |
| L66V + S394P + Y402F + T2R + RL | 11.1 |

-continued

| Enzyme | T½ |
|---|---|
| S386R + A393R + T2R | 14.1 |
| S386N + E408R | 12.6 |
| A1V + L66R + Y402F + N427S + S486G | |

T2K + S30P + N427M + S444G + V470M
A393R + T490A + V59A + PLASD(N-terminal extension)
S119P + Y312Q + Y402F + S416H,
T379A + S386K + A393R + T2E,
S386P + S340G + D357S + T360V.

Example 3

Specific Activity

AMG G2 variants were constructed as described above in Example 1. The specific activity as $k_{cat}$ or AGU/mg was measured at pH 4.5, 37° C., using maltose as substrates as described in the "Materials & Methods" section above.

| Enzyme | AGU/mg | kCat (Sec. − 1) |
|---|---|---|
| AMG G2 (wild-type) | | 5.6 |
| I189T + Y223F + F227Y + Y402F + S119P | | 9.3 |

Example 4

Thermostability at 75° C.

AMG G2 variants were constructed using the approach described in Example 1.

The thermostability was determined as T½ using method I at 75° C., ph 4.5, as described in the "Materials & Methods" section and compared to the wild-type *A. niger* AMG G2 under the same conditions.

Example 5

Saccharification Performance of AMG Variant AGR 130

Saccharification performance of the variant AGR 130 (V59A+L66R+T72I+S119P+N313G+S340G+S356G+A393R+Y402F+E408R+N427M) having improved thermostability (see Example 4) is tested at 70° C. as described below.

Reference enzyme is the wild-type *A. niger* AMG G2. Saccharification is run under the following conditions:

| | |
|---|---|
| Substrate | 10 DE Maltodextrin, approx. 30% DS (w/w) |
| Temperature | 70° C. |
| Initial pH | 4.3 (at 70° C.) |
| Enzyme dosage | 0.24 AGU/g DS |

Saccharification

The substrate for saccharification is made by dissolving maltodextrin (prepared from common corn) in boiling Milli-Q water and adjusting the dry substance to approximately PB 30% (w/w). pH is adjusted to 4.3. Aliquots of substrate corresponding to 15 g dry solids are transferred to 50 ml blue cap glass flasks and placed in a water bath with stirring. Enzymes are added and pH re-adjusted if necessary. The experiment is run in duplicate. Samples are taken periodically and analysed at HPLC for determination of the carbohydrate composition.

| AGR No. | Mutations | $T_{1/2}$ (Minutes) |
|---|---|---|
| | G2 (reference) | 4 |
| 136 | V59A + A393R + T490A | 6 |
| 109 | S56A + V59A + N313G + S356G + A393R + S394R + Y402F | 9 |
| 111 | A11E + V59A + T72I + S119P + F237H + S240G + A246T + N313G + S340G + K352R + A393R + S394R + Y402F + E408R | 10 |
| 120 | T2H + A11P + V59A + T72I + S119P + A246T + N313G + D336S + T360V + A393R + Y402F + E408R + N427M | 12 |
| 122 | T2H + V59A + T72I + S119P + S240G + N313G + T360V + S368P + A393R + Y402F + E408R + N427M | 10 |
| 124 | N9A + S56A + V59A + S119P + A246T + N313G + E342T + A393R + S394R + Y402F + E408R | 21 |
| 130 | V59A + L66R + T72I + S119P + N313G + S340G + S356G + A393R + Y402F + E408R + N427M | 29 |
| 132 | T2H + N9A + V59A + S56A + L66R + T72I + S119P + N313G + F318Y + E342T + S356G + T390R + Y402F + E408R + N427M | 9 |
| 141 | T2H + A11E + V59A + S119P + N313G + E342T + S356P + A393R + S394I + Y402F + L410R + N427S | 13 |
| 142 | T2H + A11P + V59A + S119P + N313G + S340G + S356G + E408R + N427M | 9 |
| 151 | T2H + A11E + V59A + L66R + S119P + N313G + S340G + D357S + A393R + S394R + Y402F + E408R | 20 |
| 154 | T2H + N9A + S56A + V59A + L66R + T72I + S119P + S240G + N313G + S340G + K352R + A393R + S394R + Y402F + E408R + N427S | 19 |

The invention claimed is:

1. An isolated variant of a parent glucoamylase, comprising an alteration at a position corresponding to position 342 in the amino acid sequence of SEQ ID NO: 2; wherein
   (a) the parent glucoamylase has a degree of identity of at least 95% to SEQ ID NO: 2;
   (b) the alteration is an insertion, deletion, or substitution;
   (c) the variant has 1-11 alterations relative to the parent glucoamylase; and
   (d) the variant has glucoamylase activity.

2. The variant of claim 1, which has 1-5 alterations.

3. The variant of claim 1, wherein the alterations are substitutions.

4. The variant of claim 2, wherein the alterations are substitutions.

5. The variant of claim 1, wherein the alteration at a position corresponding to position 342 is a substitution with A, R, D, N, C, Q, G, H, I, L, K, M, F, P, S, E, W, Y, or V.

6. The variant of claim 1, wherein the alteration is E342T.

7. The variant of claim 1, wherein the parent glucoamylase has a degree of identity of at least 97% to SEQ ID NO: 2.

8. The variant of claim 1, wherein the parent glucoamylase has a degree of identity of at least 99% to SEQ ID NO: 2.

9. The variant of claim 1, wherein the parent glucoamylase comprises SEQ ID NO: 2.

10. The variant of claim 1, wherein the variant has improved thermal stability when compared with the parent glucoamylase.

11. The variant of claim 1, wherein the variant has increased specific activity when compared with the parent glucoamylase.

12. The variant of claim 1, which comprises:
   N9A+S56A+V59A+S119P+A246T+N313G+E342T+ A393R+S394R+Y402F+E408R;
   S56A+V59A+S119P+A246T+N313G+E342T+A393R+ S394R+Y402F+E408R;
   V59A+S119P+A246T+N313G+E342T+A393R+ S394R+Y402F+E408R;
   S119P+A246T+N313G+E342T+A393R+S394R+ Y402F+E408R;

A246T+N313G+E342T+A393R+S394R+Y402F+
E408R;

N313G+E342T+A393R+S394R+Y402F+E408R; or

E342T+A393R+S394R+Y402F+E408R.

13. The variant of claim 1, which further comprises an alteration at one or more positions corresponding to positions 59, 66, 72, 119, 189, 223, 227, 313, 340, 352, 379, 386, 393, 395, 402, 408, 416, 425, 427, 444, 486, 490, and 494 in the amino acid sequence of SEQ ID NO: 2.

14. A process for converting starch or partially hydrolyzed starch into a syrup containing dextrose, said process comprising saccharifying the starch or partially hydrolyzed starch in the presence of a variant of claim 1.

* * * * *

SEQUENCE LISTING

<160> NUMBER OF SEQ ID NOS: 13

<210> SEQ ID NO 1
<211> LENGTH: 1605
<212> TYPE: DNA
<213> ORGANISM: Aspergillus niger
<220> FEATURE:
<221> NAME/KEY: CDS
<222> LOCATION: (1)..(1602)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1602)

<400> SEQUENCE: 1

```
atg tcg ttc cga tct cta ctc gcc ctg agc ggc ctc gtc tgc aca ggg      48
Met Ser Phe Arg Ser Leu Leu Ala Leu Ser Gly Leu Val Cys Thr Gly
            -20                 -15                 -10 ttg gca aat gtg att tcc aag cgc gcg acc ttg gat tca tgg ttg agc      96
Leu Ala Asn Val Ile Ser Lys Arg Ala Thr Leu Asp Ser Trp Leu Ser
        -5                  -1  1               5 aac gaa gcg acc gtg gct cgt act gcc atc ctg aat aac atc ggg gcg     144
Asn Glu Ala Thr Val Ala Arg Thr Ala Ile Leu Asn Asn Ile Gly Ala
         10                  15                  20 gac ggt gct tgg gtg tcg ggc gcg gac tct ggc att gtc gtt gct agt     192
Asp Gly Ala Trp Val Ser Gly Ala Asp Ser Gly Ile Val Val Ala Ser
 25                  30                  35                  40 ccc agc acg gat aac ccg gac tac ttc tac acc tgg act cgc gac tct     240
Pro Ser Thr Asp Asn Pro Asp Tyr Phe Tyr Thr Trp Thr Arg Asp Ser
                 45                  50                  55 ggt ctc gtc ctc aag acc ctc gtc gat ctc ttc cga aat gga gat acc     288
Gly Leu Val Leu Lys Thr Leu Val Asp Leu Phe Arg Asn Gly Asp Thr
             60                  65                  70 agt ctc ctc tcc acc att gag aac tac atc tcc gcc cag gca att gtc     336
Ser Leu Leu Ser Thr Ile Glu Asn Tyr Ile Ser Ala Gln Ala Ile Val
         75                  80                  85 cag ggt atc agt aac ccc tct ggt gat ctg tcc agc ggc gct ggt ctc     384
Gln Gly Ile Ser Asn Pro Ser Gly Asp Leu Ser Ser Gly Ala Gly Leu
 90                  95                 100 ggt gaa ccc aag ttc aat gtc gat gag act gcc tac act ggt tct tgg     432
Gly Glu Pro Lys Phe Asn Val Asp Glu Thr Ala Tyr Thr Gly Ser Trp
105                 110                 115                 120 gga cgg ccg cag cga gat ggt ccg gct ctg aga gca act gct atg atc     480
Gly Arg Pro Gln Arg Asp Gly Pro Ala Leu Arg Ala Thr Ala Met Ile
                125                 130                 135 ggc ttc ggg cag tgg ctg ctt gac aat ggc tac acc agc acc gca acg     528
Gly Phe Gly Gln Trp Leu Leu Asp Asn Gly Tyr Thr Ser Thr Ala Thr
            140                 145                 150 gac att gtt tgg ccc ctc gtt agg aac gac ctg tcg tat gtg gct caa     576
Asp Ile Val Trp Pro Leu Val Arg Asn Asp Leu Ser Tyr Val Ala Gln
        155                 160                 165 tac tgg aac cag aca gga tat gat ctc tgg gaa gaa gtc aat ggc tcg     624
Tyr Trp Asn Gln Thr Gly Tyr Asp Leu Trp Glu Glu Val Asn Gly Ser
    170                 175                 180 tct ttc ttt acg att gct gtg caa cac cgc gcc ctt gtc gaa ggt agt     672
Ser Phe Phe Thr Ile Ala Val Gln His Arg Ala Leu Val Glu Gly Ser
185                 190                 195                 200 gcc ttc gcg acg gcc gtc ggc tcg tcc tgc tcc tgg tgt gat tct cag     720
Ala Phe Ala Thr Ala Val Gly Ser Ser Cys Ser Trp Cys Asp Ser Gln
                205                 210                 215
```

```
gca ccc gaa att ctc tgc tac ctg cag tcc ttc tgg acc ggc agc ttc      768
Ala Pro Glu Ile Leu Cys Tyr Leu Gln Ser Phe Trp Thr Gly Ser Phe
        220                 225                 230 att ctg gcc aac ttc gat agc agc cgt tcc ggc aag gac gca aac acc      816
Ile Leu Ala Asn Phe Asp Ser Ser Arg Ser Gly Lys Asp Ala Asn Thr
            235                 240                 245 ctc ctg gga agc atc cac acc ttt gat cct gag gcc gca tgc gac gac      864
Leu Leu Gly Ser Ile His Thr Phe Asp Pro Glu Ala Ala Cys Asp Asp
250                 255                 260 tcc acc ttc cag ccc tgc tcc ccg cgc gcg ctc gcc aac cac aag gag      912
Ser Thr Phe Gln Pro Cys Ser Pro Arg Ala Leu Ala Asn His Lys Glu
265                 270                 275                 280 gtt gta gac tct ttc cgc tca atc tat acc ctc aac gat ggt ctc agt      960
Val Val Asp Ser Phe Arg Ser Ile Tyr Thr Leu Asn Asp Gly Leu Ser
                285                 290                 295 gac agc gag gct gtt gcg gtg ggt cgg tac cct gag gac acg tac tac     1008
Asp Ser Glu Ala Val Ala Val Gly Arg Tyr Pro Glu Asp Thr Tyr Tyr
                    300                 305                 310 aac ggc aac ccg tgg ttc ctg tgc acc ttg gct gcc gca gag cag ttg     1056
Asn Gly Asn Pro Trp Phe Leu Cys Thr Leu Ala Ala Ala Glu Gln Leu
                315                 320                 325 tac gat gct cta tac cag tgg gac aag cag ggg tcg ttg gag gtc aca     1104
Tyr Asp Ala Leu Tyr Gln Trp Asp Lys Gln Gly Ser Leu Glu Val Thr
        330                 335                 340 gat gtg tcg ctg gac ttc ttc aag gca ctg tac agc gat gct gct act     1152
Asp Val Ser Leu Asp Phe Phe Lys Ala Leu Tyr Ser Asp Ala Ala Thr
345                 350                 355                 360 ggc acc tac tct tcg tcc agt tcg act tat agt agc att gta gat gcc     1200
Gly Thr Tyr Ser Ser Ser Ser Ser Thr Tyr Ser Ser Ile Val Asp Ala
                365                 370                 375 gtg aag act ttc gcc gat ggc ttc gtc tct att gtg gaa act cac gcc     1248
Val Lys Thr Phe Ala Asp Gly Phe Val Ser Ile Val Glu Thr His Ala
                    380                 385                 390 gca agc aac ggc tcc atg tcc gag caa tac gac aag tct gat ggc gag     1296
Ala Ser Asn Gly Ser Met Ser Glu Gln Tyr Asp Lys Ser Asp Gly Glu
                395                 400                 405 cag ctt tcc gct cgc gac ctg acc tgg tct tat gct gct ctg ctg acc     1344
Gln Leu Ser Ala Arg Asp Leu Thr Trp Ser Tyr Ala Ala Leu Leu Thr
        410                 415                 420 gcc aac aac cgt cgt aac tcc gtc gtg cct gct tct tgg ggc gag acc     1392
Ala Asn Asn Arg Arg Asn Ser Val Val Pro Ala Ser Trp Gly Glu Thr
425                 430                 435                 440 tct gcc agc agc gtg ccc ggc acc tgt gcg gcc aca tct gcc att ggt     1440
Ser Ala Ser Ser Val Pro Gly Thr Cys Ala Ala Thr Ser Ala Ile Gly
                445                 450                 455 acc tac agc agt gtg act gtc acc tcg tgg ccg agt atc gtg gct act     1488
Thr Tyr Ser Ser Val Thr Val Thr Ser Trp Pro Ser Ile Val Ala Thr
                    460                 465                 470 ggc ggc acc act acg acg gct acc ccc act gga tcc ggc agc gtg acc     1536
Gly Gly Thr Thr Thr Thr Ala Thr Pro Thr Gly Ser Gly Ser Val Thr
                475                 480                 485 tcg acc agc aag acc acc gcg act gct agc aag acc agc acc acg acc     1584
Ser Thr Ser Lys Thr Thr Ala Thr Ala Ser Lys Thr Ser Thr Thr Thr
        490                 495                 500 cgc tct ggt atg tca ctg tga                                         1605
Arg Ser Gly Met Ser Leu
505                 510

<210> SEQ ID NO 2
<211> LENGTH: 534
```

<212> TYPE: PRT
<213> ORGANISM: Aspergillus niger

<400> SEQUENCE: 2

```
Met Ser Phe Arg Ser Leu Leu Ala Leu Ser Gly Leu Val Cys Thr Gly
            -20                 -15                 -10

Leu Ala Asn Val Ile Ser Lys Arg Ala Thr Leu Asp Ser Trp Leu Ser
             -5              -1   1                  5

Asn Glu Ala Thr Val Ala Arg Thr Ala Ile Leu Asn Asn Ile Gly Ala
         10                  15                  20

Asp Gly Ala Trp Val Ser Gly Ala Asp Ser Gly Ile Val Val Ala Ser
 25                  30                  35                  40

Pro Ser Thr Asp Asn Pro Asp Tyr Phe Tyr Thr Trp Thr Arg Asp Ser
                 45                  50                  55

Gly Leu Val Leu Lys Thr Leu Val Asp Leu Phe Arg Asn Gly Asp Thr
                 60                  65                  70

Ser Leu Leu Ser Thr Ile Glu Asn Tyr Ile Ser Ala Gln Ala Ile Val
             75                  80                  85

Gln Gly Ile Ser Asn Pro Ser Gly Asp Leu Ser Ser Gly Ala Gly Leu
 90                  95                 100

Gly Glu Pro Lys Phe Asn Val Asp Glu Thr Ala Tyr Thr Gly Ser Trp
105                 110                 115                 120

Gly Arg Pro Gln Arg Asp Gly Pro Ala Leu Arg Ala Thr Ala Met Ile
                125                 130                 135

Gly Phe Gly Gln Trp Leu Leu Asp Asn Gly Tyr Thr Ser Thr Ala Thr
                140                 145                 150

Asp Ile Val Trp Pro Leu Val Arg Asn Asp Leu Ser Tyr Val Ala Gln
            155                 160                 165

Tyr Trp Asn Gln Thr Gly Tyr Asp Leu Trp Glu Glu Val Asn Gly Ser
170                 175                 180

Ser Phe Phe Thr Ile Ala Val Gln His Arg Ala Leu Val Glu Gly Ser
185                 190                 195                 200

Ala Phe Ala Thr Ala Val Gly Ser Ser Cys Ser Trp Cys Asp Ser Gln
                205                 210                 215

Ala Pro Glu Ile Leu Cys Tyr Leu Gln Ser Phe Trp Thr Gly Ser Phe
                220                 225                 230

Ile Leu Ala Asn Phe Asp Ser Ser Arg Ser Gly Lys Asp Ala Asn Thr
            235                 240                 245

Leu Leu Gly Ser Ile His Thr Phe Asp Pro Glu Ala Ala Cys Asp Asp
            250                 255                 260

Ser Thr Phe Gln Pro Cys Ser Pro Arg Ala Leu Ala Asn His Lys Glu
265                 270                 275                 280

Val Val Asp Ser Phe Arg Ser Ile Tyr Thr Leu Asn Asp Gly Leu Ser
                285                 290                 295

Asp Ser Glu Ala Val Ala Val Gly Arg Tyr Pro Glu Asp Thr Tyr Tyr
                300                 305                 310

Asn Gly Asn Pro Trp Phe Leu Cys Thr Leu Ala Ala Ala Glu Gln Leu
                315                 320                 325

Tyr Asp Ala Leu Tyr Gln Trp Asp Lys Gln Gly Ser Leu Glu Val Thr
            330                 335                 340

Asp Val Ser Leu Asp Phe Phe Lys Ala Leu Tyr Ser Asp Ala Ala Thr
345                 350                 355                 360

Gly Thr Tyr Ser Ser Ser Ser Ser Thr Tyr Ser Ser Ile Val Asp Ala
                365                 370                 375
```

-continued

```
Val Lys Thr Phe Ala Asp Gly Phe Val Ser Ile Val Glu Thr His Ala
            380                 385                 390
Ala Ser Asn Gly Ser Met Ser Glu Gln Tyr Asp Lys Ser Asp Gly Glu
        395                 400                 405
Gln Leu Ser Ala Arg Asp Leu Thr Trp Ser Tyr Ala Ala Leu Leu Thr
    410                 415                 420
Ala Asn Asn Arg Arg Asn Ser Val Val Pro Ala Ser Trp Gly Glu Thr
425                 430                 435                 440
Ser Ala Ser Ser Val Pro Gly Thr Cys Ala Ala Thr Ser Ala Ile Gly
                445                 450                 455
Thr Tyr Ser Ser Val Thr Val Thr Ser Trp Pro Ser Ile Val Ala Thr
                460                 465                 470
Gly Gly Thr Thr Thr Thr Ala Thr Pro Thr Gly Ser Gly Ser Val Thr
            475                 480                 485
Ser Thr Ser Lys Thr Thr Ala Thr Ala Ser Lys Thr Ser Thr Thr Thr
        490                 495                 500
Arg Ser Gly Met Ser Leu
505                 510

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gaatgacttg gttgacgcgt caccagtcac                                      30

<210> SEQ ID NO 4
<211> LENGTH: 68
<212> TYPE: DNA
<213> ORGANISM: Artificial Sequence
<220> FEATURE:
<223> OTHER INFORMATION: Primer

<400> SEQUENCE: 4
ggggatcatg ataggactag ccatattaat gaagggcata taccacgcct tggacctgcg      60
ttatagcc                                                              68

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
gcaacgaagc gcccgtggct cgtac                                           25

<210> SEQ ID NO 6
<211> LENGTH: 88
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (44)..(44)
<223> OTHER INFORMATION: n denotes A, G, C or T

<400> SEQUENCE: 6
cgaagcgacc gtggctcgta ctgccatcta taacatcggc gcgtctgtgc gcggtggcat      60
```

```
tgtcgttgct agtcccagca cggataac                                               88

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gatggcagta cgagccacgg tcgcttcg                                               28

<210> SEQ ID NO 8
<211> LENGTH: 75
<212> TYPE: DNA
<213> ORGANISM: Artificial Sequence
<220> FEATURE:
<223> OTHER INFORMATION: Primer

<400> SEQUENCE: 8
gtgtcgctgg acttcttcaa gaacctctta ccctactaca gtcgttatca ttgatgccgt           60
gaagactttc gccga                                                            75

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cttgaagaag tccagcgaca c                                                     21

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
catccccagg atccttactc agcaatg                                               27

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
ctcaaacgac tcaccagcct ctagagt                                               27

<210> SEQ ID NO 12
<211> LENGTH: 2602
<212> TYPE: DNA
<213> ORGANISM: Aspergillus niger

<400> SEQUENCE: 12
ttcgtcgcct aatgtctcgt ccgttcacaa actgaagagc ttgaagtggc gagatgtctc           60
tgcaggaatt caagctagat gctaagcgat attgcatggc aatatgtgtt gatgcatgtg          120
cttcttcctt cagcttcccc tcgtgcgagt gaggtttggc tataaattga agtggttggt          180
cggggttccg tgaggggctg aagtgcttcc tcccttttag gcgcaactga gagcctgagc          240
```

-continued

| | |
|---|---|
| ttcatcccca gcatcattac acctcagcaa tgtcgttccg atctctactc gccctgagcg | 300 |
| gcctcgtctg cacagggttg gcaaatgtga tttccaagcg cgcgaccttg gattcatggt | 360 |
| tgagcaacga agcgaccgtg gctcgtactg ccatcctgaa taacatcggg gcggacggtg | 420 |
| cttgggtgtc gggcgcggac tctggcattg tcgttgctag tcccagcacg gataacccgg | 480 |
| actgtatgtt tcgagctcag atttagtatg agtgtgtcat tgattgattg atgctgactg | 540 |
| gcgtgtcgtt tgttgtagac ttctacacct ggactcgcga ctctggtctc gtcctcaaga | 600 |
| ccctcgtcga tctcttccga aatggagata ccagtctcct ctccaccatt gagaactaca | 660 |
| tctccgccca ggcaattgtc cagggtatca gtaacccctc tggtgatctg tccagcggcg | 720 |
| ctggtctcgg tgaacccaag ttcaatgtcg atgagactgc ctacactggt tcttggggac | 780 |
| ggccgcagcg agatggtccg gctctgagag caactgctat gatcggcttc gggcagtggc | 840 |
| tgcttgtatg ttctccaccc ccttgcgtct gatctgtgac atatgtagct gactggtcag | 900 |
| gacaatggct acaccagcac cgcaacggac attgtttggc ccctcgttag gaacgacctg | 960 |
| tcgtatgtgg ctcaatactg gaaccagaca ggatatggtg tgtttgtttt attttaaatt | 1020 |
| tccaaagatg cgccagcaga gctaacccgc gatcgcagat ctctgggaag aagtcaatgg | 1080 |
| ctcgtctttc tttacgattg ctgtgcaaca ccgcgccctt gtcgaaggta gtgccttcgc | 1140 |
| gacggccgtc ggctcgtcct gctcctggtg tgattctcag gcacccgaaa ttctctgcta | 1200 |
| cctgcagtcc ttctggaccg gcagcttcat tctggccaac ttcgatagca gccgttccgg | 1260 |
| caaggacgca aacaccctcc tgggaagcat ccacaccttt gatcctgagg ccgcatgcga | 1320 |
| cgactccacc ttccagcccct gctcccgcg cgcgctcgcc aaccacaagg aggttgtaga | 1380 |
| ctcttttccgc tcaatctata ccctcaacga tggtctcagt gacagcgagg ctgttgcggt | 1440 |
| gggtcggtac cctgaggaca cgtactacaa cggcaacccg tggttcctgt gcaccttggc | 1500 |
| tgccgcagag cagttgtacg atgctctata ccagtgggac aagcaggggt cgttggaggt | 1560 |
| cacagatgtg tcgctggact tcttcaaggc actgtacagc gatgctgcta ctggcaccta | 1620 |
| ctcttcgtcc agttcgactt atagtagcat tgtagatgcc gtgaagactt cgccgatgg | 1680 |
| cttcgtctct attgtggtaa gtctacgcta gacaagcgct catgttgaca gagggtgcgt | 1740 |
| actaacagaa gtaggaaact cacgccgcaa gcaacggctc catgtccgag caatacgaca | 1800 |
| agtctgatgg cgagcagctt tccgctcgcg acctgacctg gtcttatgct gctctgctga | 1860 |
| ccgccaacaa ccgtcgtaac tccgtcgtgc ctgcttcttg gggcgagacc tctgccagca | 1920 |
| gcgtgcccgg cacctgtgcg gccacatctg ccattggtac ctacagcagt gtgactgtca | 1980 |
| cctcgtggcc gagtatcgtg gctactgcg gcaccactac gacggctacc cccactggat | 2040 |
| ccggcagcgt gacctcgacc agcaagacca ccgcgactgc tagcaagacc agcaccagta | 2100 |
| cgtcatcaac ctcctgtacc actcccaccg ccgtggctgt gactttcgat ctgacagcta | 2160 |
| ccaccaccta cggcgagaac atctacctgg tcggatcgat ctctcagctg ggtgactggg | 2220 |
| aaaccagcga cggcatagct ctgagtgctg acaagtacac ttccagcgac ccgctctggt | 2280 |
| atgtcactgt gactctgccg gctggtgagt cgtttgagta caagtttatc cgcattgaga | 2340 |
| gcgatgactc cgtggagtgg gagagtgatc ccaaccgaga atacaccgtt cctcaggcgt | 2400 |
| gcggaacgtc gaccgcgacg gtgactgaca cctggcggtg acaatcaatc catttcgcta | 2460 |
| tagttaaagg atggggatga gggcaattgg ttatatgatc atgtatgtag tgggtgtgca | 2520 |
| taatagtagt gaaatggaag ccaagtcatg tgattgtaat cgaccgacgg aattgaggat | 2580 |
| atccggaaat acagacaccg gg | 2602 |

<210> SEQ ID NO 13
<211> LENGTH: 640
<212> TYPE: PRT
<213> ORGANISM: Aspergillus niger

<400> SEQUENCE: 13

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
                20                  25                  30

Asn Glu Ala Thr Val Ala Arg Thr Ala Ile Leu Asn Asn Ile Gly Ala
            35                  40                  45

Asp Gly Ala Trp Val Ser Gly Ala Asp Ser Gly Ile Val Val Ala Ser
        50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
                100                 105                 110

Gln Gly Ile Ser Asn Pro Ser Gly Asp Leu Ser Ser Gly Ala Gly Leu
            115                 120                 125

Gly Glu Pro Lys Phe Asn Val Asp Glu Thr Ala Tyr Thr Gly Ser Trp
130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350
```

```
                                -continued

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640
```